(12) United States Patent
Hoffman (10) Patent No.: US 10,646,176 B2
(45) Date of Patent: May 12, 2020

(54) LAYERED RADIATION DETECTOR

(71) Applicant: GENERAL ELECTRIC COMPANY, Schenectady, NY (US)

(72) Inventor: David Michael Hoffman, New Berlin, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 660 days.

(21) Appl. No.: 14/871,596

(22) Filed: Sep. 30, 2015

(65) Prior Publication Data
US 2017/0090039 A1    Mar. 30, 2017

(51) Int. Cl.
| | | |
|---|---|---|
| *A61B 6/03* | (2006.01) | |
| *G01T 1/24* | (2006.01) | |
| *A61B 6/00* | (2006.01) | |
| *G01T 1/16* | (2006.01) | |
| *G01T 1/20* | (2006.01) | |
| *G01T 1/29* | (2006.01) | |

(52) U.S. Cl.
CPC ............ *A61B 6/4241* (2013.01); *A61B 6/032* (2013.01); *A61B 6/42* (2013.01); *A61B 6/4208* (2013.01); *A61B 6/4233* (2013.01); *A61B 6/4266* (2013.01); *A61B 6/4291* (2013.01); *A61B 6/482* (2013.01); *A61B 6/5205* (2013.01); *G01T 1/1603* (2013.01); *G01T 1/2006* (2013.01); *G01T 1/2018* (2013.01); *G01T 1/24* (2013.01); *G01T 1/242* (2013.01); *G01T 1/2985* (2013.01)

(58) Field of Classification Search
CPC ..... A61B 6/032; A61B 6/4208; A61B 6/4233; A61B 6/4241; A61B 6/42; A61B 6/4266; A61B 6/4291; A61B 6/482; G01T 1/24; G01T 1/242
USPC ................ 378/19, 98.8, 5, 98.9; 250/370.09
See application file for complete search history.

(56) References Cited

U.S. PATENT DOCUMENTS

| | | | | |
|---|---|---|---|---|
| 4,870,667 | A  * | 9/1989 | Brunnett | ............... G01T 1/2018 250/367 |
| 5,799,057 | A  | 8/1998 | Hoffman et al. | |
| 6,005,908 | A  * | 12/1999 | Oppelt | ................. G01T 1/2985 378/11 |
| 6,134,301 | A  | 10/2000 | Mruzek et al. | |
| 6,272,207 | B1 * | 8/2001 | Tang | ..................... G21K 1/025 378/149 |
| 6,396,898 | B1 * | 5/2002 | Saito | .................... G01N 23/046 378/19 |
| 6,473,486 | B2 * | 10/2002 | Hoffman | ................ A61B 6/032 250/367 |
| 6,512,809 | B2 * | 1/2003 | Doubrava | ......... H01L 27/14663 250/370.09 |

(Continued)

*Primary Examiner* — Allen C. Ho
(74) *Attorney, Agent, or Firm* — Fletcher Yoder, P.C.

(57) ABSTRACT

A radiation detector having an energy-integrating detection layer and at least one direct-conversion detection layer is described. In certain embodiments, the direct-conversion layer is impacted first by an incident X-ray beam, such that X-ray photons stopped at the direct-conversion layer are generally lower in energy than those which reach the energy-integrating detection layer. The data acquired using the direct-conversion layers and energy-integrating layers may be combined to provide additional spectral discrimination, such as in material decomposition or contrast-enhancement applications.

9 Claims, 6 Drawing Sheets

(56) References Cited

U.S. PATENT DOCUMENTS

| | | | |
|---|---|---|---|
| 6,553,092 B1 * | 4/2003 | Mattson | G01T 1/2018 250/370.11 |
| 6,567,495 B2 | 5/2003 | McGrath et al. | |
| 6,707,046 B2 | 3/2004 | Possin et al. | |
| 6,778,637 B2 * | 8/2004 | Luhta | G21K 1/025 250/363.1 |
| 6,933,504 B2 | 8/2005 | Hoffman et al. | |
| 6,980,629 B1 * | 12/2005 | Hoheisel | G21K 1/025 264/401 |
| 6,982,423 B2 * | 1/2006 | Elgali | G01T 1/1648 250/370.11 |
| 7,064,334 B2 | 6/2006 | Hoffman et al. | |
| 7,082,183 B2 | 7/2006 | Toth et al. | |
| 7,084,404 B2 | 8/2006 | Hoffman et al. | |
| 7,149,283 B2 * | 12/2006 | Hoheisel | G21K 1/025 378/149 |
| 7,166,849 B2 | 1/2007 | Jiang et al. | |
| 7,173,998 B2 | 2/2007 | Hoffman et al. | |
| 7,209,536 B2 * | 4/2007 | Walter | A61B 6/032 378/5 |
| 7,212,604 B2 | 5/2007 | Tkaczyk | G01T 1/2985 378/19 |
| 7,236,560 B2 * | 6/2007 | Malamud | A61B 6/032 250/505.1 |
| 7,238,945 B2 | 7/2007 | Hoffman et al. | |
| 7,260,174 B2 * | 8/2007 | Hoffman | A61B 6/032 250/363.09 |
| 7,282,713 B2 | 10/2007 | Jiang et al. | |
| 7,283,608 B2 | 10/2007 | Hoffman | |
| 7,289,336 B2 | 10/2007 | Burdick et al. | |
| 7,324,623 B2 * | 1/2008 | Heuscher | A61B 6/032 378/16 |
| 7,366,279 B2 * | 4/2008 | Edic | A61B 6/032 378/150 |
| 7,372,934 B2 * | 5/2008 | De Man | A61B 6/032 250/370.09 |
| 7,382,854 B2 | 6/2008 | Hoffman et al. | |
| 7,439,516 B2 | 10/2008 | Zeman et al. | |
| 7,442,938 B2 | 10/2008 | Jiang et al. | |
| 7,466,793 B2 * | 12/2008 | Wu | A61B 6/032 378/19 |
| 7,479,639 B1 * | 1/2009 | Shahar | G01T 1/17 250/370.06 |
| 7,512,210 B2 * | 3/2009 | Possin | A61B 6/032 250/370.09 |
| 7,525,097 B2 * | 4/2009 | Dorscheid | G01T 1/2018 250/370.09 |
| 7,532,703 B2 * | 5/2009 | Du | A61B 6/032 378/116 |
| 7,545,904 B2 | 6/2009 | Hoffman | |
| 7,560,702 B2 | 7/2009 | Meirav et al. | |
| 7,564,940 B2 * | 7/2009 | Mattson | A61B 6/032 250/370.09 |
| 7,573,040 B2 * | 8/2009 | Tkaczyk | G01T 1/249 250/370.09 |
| 7,545,902 B2 | 9/2009 | Hoffman | |
| 7,583,779 B2 * | 9/2009 | Tkaczyk | A61B 6/032 378/4 |
| 7,586,252 B2 | 9/2009 | Bueno et al. | |
| 7,590,215 B2 * | 9/2009 | Schlomka | A61B 6/032 378/4 |
| 7,593,502 B2 | 9/2009 | Katcha et al. | |
| 7,606,347 B2 * | 10/2009 | Tkaczyk | A61B 6/032 378/19 |
| 7,609,804 B2 | 10/2009 | Hoffman et al. | |
| 7,613,274 B2 * | 11/2009 | Tkaczyk | A61B 6/032 378/19 |
| 7,615,161 B2 | 11/2009 | Hoffman | |
| 7,696,481 B2 * | 4/2010 | Tkaczyk | G01T 1/2985 250/363.02 |
| 7,697,657 B2 * | 4/2010 | Walter | A61B 6/4241 378/4 |
| 7,724,865 B2 * | 5/2010 | Wu | A61B 6/032 378/4 |
| 7,734,076 B2 * | 6/2010 | Du | A61B 6/032 378/16 |
| 7,826,587 B1 * | 11/2010 | Langan | A61B 6/032 378/16 |
| 7,829,860 B2 * | 11/2010 | Nygard | G01T 1/2018 250/366 |
| 7,885,372 B2 * | 2/2011 | Edic | A61B 6/032 378/158 |
| 7,935,933 B2 | 5/2011 | Hoffman | |
| 7,974,377 B2 | 7/2011 | Hoffman et al. | |
| 8,055,039 B2 * | 11/2011 | Wu | G06T 5/002 382/128 |
| 8,077,826 B2 * | 12/2011 | Ruimi | A61B 6/032 378/19 |
| 8,111,803 B2 * | 2/2012 | Edic | A61B 6/4035 378/146 |
| 8,199,874 B2 * | 6/2012 | Toth | A61B 6/032 378/16 |
| 8,199,875 B2 * | 6/2012 | Chandra | A61B 6/032 378/16 |
| 8,311,182 B2 * | 11/2012 | Chandra | A61B 6/03 378/5 |
| 8,315,352 B2 * | 11/2012 | Wu | A61B 6/032 378/18 |
| 8,373,135 B2 * | 2/2013 | Kappler | G01T 1/247 250/336.1 |
| 8,378,310 B2 * | 2/2013 | Bornefalk | G06T 11/005 250/370.01 |
| 8,384,038 B2 * | 2/2013 | Guo | G01T 1/247 250/370.09 |
| 8,422,636 B2 * | 4/2013 | Greenberg | G01T 7/005 378/207 |
| 8,442,184 B2 * | 5/2013 | Forthmann | A61B 6/032 378/5 |
| 8,483,352 B2 | 7/2013 | Hoffman et al. | |
| 8,483,353 B2 | 7/2013 | Hoffman et al. | |
| 8,488,736 B2 | 7/2013 | Hoffman et al. | |
| 8,513,613 B2 * | 8/2013 | Herrmann | G01T 1/20 250/370.09 |
| 8,581,200 B2 * | 11/2013 | Engel | G01T 1/2928 250/370.09 |
| 8,761,333 B2 | 6/2014 | Ikhlef et al. | |
| 8,787,519 B2 * | 7/2014 | Fan | A61B 6/032 378/5 |
| 8,873,703 B2 * | 10/2014 | Ruimi | A61B 6/032 250/370.09 |
| 8,913,711 B2 * | 12/2014 | Moriyasu | A61B 6/03 378/4 |
| 8,988,267 B1 * | 3/2015 | Kimura | G01T 1/2928 341/155 |
| 9,014,455 B2 * | 4/2015 | Oh | A61B 6/52 378/98.11 |
| 9,116,248 B2 * | 8/2015 | Abenaim | A61B 6/032 |
| 9,135,728 B2 * | 9/2015 | Fan | A61B 6/06 |
| 9,160,939 B2 * | 10/2015 | Funaki | H03M 1/145 |
| 9,239,391 B2 * | 1/2016 | Han | G01T 1/17 |
| 9,254,113 B2 * | 2/2016 | Kim | A61B 6/4241 |
| 9,268,038 B2 * | 2/2016 | Hoffman | G01T 1/2002 |
| 9,274,235 B2 * | 3/2016 | Kang | G01N 23/04 |
| 9,310,490 B2 * | 4/2016 | Abraham | G01T 1/17 |
| 9,310,495 B2 * | 4/2016 | Spartiotis | G01T 1/247 |
| 9,316,745 B2 * | 4/2016 | Noshi | A61B 6/4241 |
| 9,389,320 B2 * | 7/2016 | Ogawa | A61B 6/14 |
| 9,408,585 B2 * | 8/2016 | Oh | A61B 6/482 |
| 9,417,339 B2 * | 8/2016 | Spahn | G01T 1/247 |
| 9,423,515 B2 * | 8/2016 | Roessl | G01T 1/241 |
| 9,423,517 B2 * | 8/2016 | Kang | G01T 1/169 |
| 9,433,391 B2 * | 9/2016 | Miyazaki | A61B 6/4241 |
| 9,437,016 B2 * | 9/2016 | Rigie | G06T 11/008 |
| 9,480,444 B2 * | 11/2016 | Kappler | A61B 6/032 |
| 9,488,739 B2 * | 11/2016 | Pelc | G01T 1/247 |
| 9,504,439 B2 * | 11/2016 | Yi | A61B 6/5205 |
| 9,517,045 B2 * | 12/2016 | Kang | G01N 23/087 |
| 9,526,466 B2 * | 12/2016 | Karim | A61B 6/4241 |
| 9,535,172 B2 * | 1/2017 | Lee | G01T 1/24 |

(56) References Cited

U.S. PATENT DOCUMENTS

| | | | |
|---|---|---|---|
| 9,579,075 B2* | 2/2017 | Besson | G01T 1/2985 |
| 9,588,239 B2* | 3/2017 | Abraham | G01T 1/247 |
| 9,595,101 B2* | 3/2017 | Kato | G06T 11/005 |
| 9,601,223 B2* | 3/2017 | Deych | G21K 1/025 |
| 9,603,577 B2* | 3/2017 | Oh | A61B 6/484 |
| 9,619,730 B2* | 4/2017 | Pavlovich | A61B 6/5205 |
| 9,645,260 B2* | 5/2017 | Abraham | G01T 1/247 |
| 9,668,706 B2* | 6/2017 | Kim | A61B 6/563 |
| 9,675,309 B2* | 6/2017 | Kim | A61B 6/4266 |
| 9,678,220 B2* | 6/2017 | Herrmann | G01T 1/17 |
| 9,693,743 B2* | 7/2017 | Arakita | G01T 1/1606 |
| 9,700,268 B2* | 7/2017 | Kang | A61B 6/542 |
| 9,730,665 B2* | 8/2017 | Choi | A61B 6/5264 |
| 9,753,154 B2* | 9/2017 | Hackenschmied | G01T 1/2002 |
| 9,757,088 B2* | 9/2017 | Roberts | A61B 6/547 |
| 9,808,210 B2* | 11/2017 | Yamazaki | A61B 6/032 |
| 9,826,944 B2* | 11/2017 | Kobayashi | A61B 6/06 |
| 9,872,661 B2* | 1/2018 | Ono | A61B 6/5205 |
| 9,877,689 B2* | 1/2018 | Kawata | G01T 1/17 |
| 9,907,528 B2* | 3/2018 | Yi | A61B 6/5282 |
| 9,924,916 B2* | 3/2018 | Kato | A61B 6/4241 |
| 9,958,556 B1* | 5/2018 | Verbakel | G01T 1/241 |
| 9,968,314 B1* | 5/2018 | Sebring | A61B 6/4233 |
| 10,007,012 B2* | 6/2018 | Nakayama | A61B 6/42 |
| 10,034,652 B2* | 7/2018 | Cho | A61B 6/585 |
| 10,154,821 B2* | 12/2018 | Kawata | A61B 6/032 |
| 10,159,450 B2* | 12/2018 | Kato | A61B 6/52 |
| 10,206,638 B2* | 2/2019 | Nakai | A61B 6/4241 |
| 10,281,592 B2* | 5/2019 | Kawata | G01T 1/17 |
| 10,295,678 B2* | 5/2019 | Tanabe | G01T 1/20 |
| 10,426,417 B2* | 10/2019 | Grass | A61B 6/5205 |
| 10,539,687 B2* | 1/2020 | Deych | A61B 6/032 |
| 2007/0076842 A1 | 4/2007 | Tkaczyk et al. | |
| 2014/0048712 A1 | 2/2014 | Hoffman | |

* cited by examiner

LAYERED RADIATION DETECTOR

BACKGROUND

The subject matter disclosed herein relates to relates to a multi-layer radiation detector configuration, with each layer providing different information regarding the incident radiation.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photo detector produces signals representative of the amount or intensity of radiation impacting discrete pixel regions of a detector surface. The signals may then be processed to generate an image that may be displayed for review. In CT systems a detector array, including a series of detector elements, produces similar signals through various positions as a gantry is displaced around a patient.

In the images produced by such systems, the internal structures and organs within a patient's body may be identified and their structure examined. It may also be desirable to characterize the tissues or agents that are present in the imaged volume, such as based on tissue type or the presence or absence of a chemical or molecule of interest, such as a contrast agent. However, in practice, such characterization may be difficult to achieve. In particular, in conventional computed tomography (CT), the X-ray attenuation proximity of multiple tissues at any given energy may make tissue classification difficult to achieve. That is, although materials have a distinct attenuation profile across different energies, tissue separation is not trivial as tissues are a mixture of different materials with range of densities and atomic number that vary across subjects.

Based on these difficulties, various approaches have been attempted for improving such tissue or chemical characterization within acquired images. Examples of such techniques often utilize X-ray emission at multiple, different spectra, such as two spectra with one spectrum characterized as a high energy relative to the other, low energy spectrum. However, in practice, such multi-spectral imaging approaches are still inadequate at providing good energy discrimination, thus limiting the applicability and usefulness of these approaches.

BRIEF DESCRIPTION

In one embodiment, a radiation detector is provided. In accordance with this embodiment, the radiation detector includes an energy-integrating detection layer having: a scintillator layer that generates optical photons when exposed to a beam of X-rays; and an imager layer positioned to generate a first set of measurements when exposed to optical photons generated by the scintillator layer. The radiation detector also includes a direct-conversion photon counting detection layer where each X-ray is individually detected and its energy is measured, configured to generate a second set of measurements when exposed to the beam of X-rays. The direct conversion detection layer is positioned relative to the energy-integrating detection layer so as to be impacted by the X-ray beam before the energy-integrating detection layer.

In a further embodiment, an imaging system is provided. In accordance with this embodiment, the imaging system includes one or more X-ray sources configured to emit X-rays across an imaging volume, an X-ray detector, and a system controller configured to control operation of one or both of the X-ray source and the X-ray detector. The X-ray detector includes an energy-integrating detection layer configured to generate a first set of measurements in response to emitted X-rays; and a direct-conversion detection layer configured to generate a first set of measurements in response to emitted X-rays. The imaging system also includes one or more processor-based components configured to generate images using both the first set of measurements and the second set of measurements.

In an additional embodiment, a radiation detection method is provided. In accordance with this embodiment, X-rays are emitted through an imaging volume and toward an X-ray detector. The X-ray detector comprises an energy-integrating layer and at least one direct-conversion layer. A first set of measurements are acquired from the at least one direct-conversion layer. The first set of measurements generally correspond to lower energy X-rays. A second set of measurements are acquired from the energy-integrating detector. An image is generated using both the first set of measurements and the second set of measurements.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with systemrelated and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of passengers, visitors, packages, boxes, luggage, and so forth (i.e., security or screening applications). In general, the present approaches may be desirable in any imaging or screening context in which material decomposition is desirable.

By way of example, in a medical context tissue characterization or classification may be desirable in various clinical applications to assess the tissue being characterized for pathological conditions and/or to assess the tissue for the presence of various elements, chemicals or molecules of interest. However, tissue characterization in imaging studies, such as using computed tomography (CT), may be problematic due to tissues being a mixture of different materials with range of densities that vary across subjects. In particular, the difficulty in distinguishing X-ray detection events of different energy levels limits the usefulness of such material decomposition or differentiation approaches.

Figure 1:
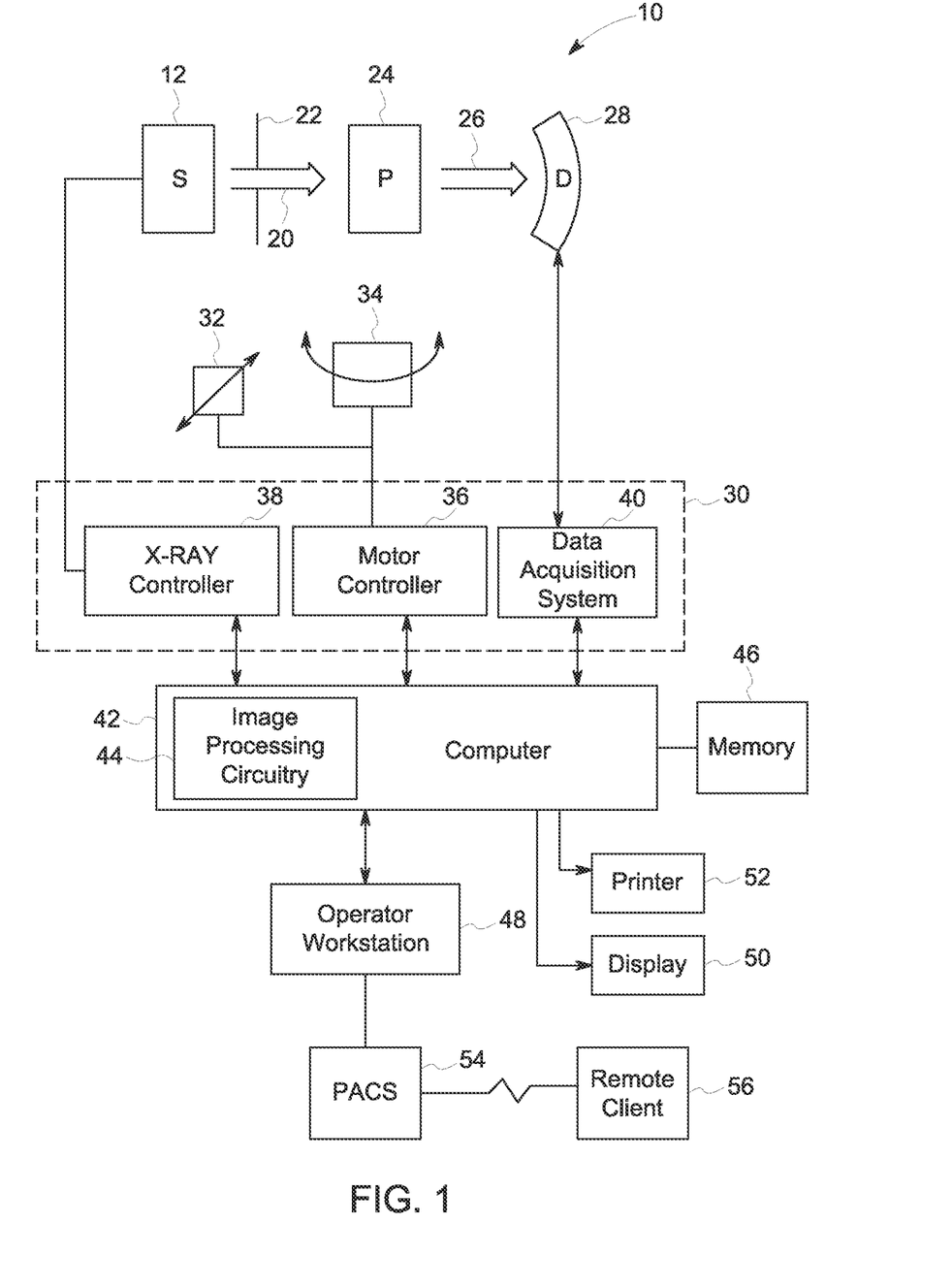
FIG. 1 is a schematic illustration of an embodiment of a computed tomography (CT) system configured to acquire CT images of a patient and process the images in accordance with aspects of the present disclosure.

Prior to discussing certain approaches for improving such material decomposition applications, it may be useful to understand the operation and components of an imaging system that may be used to acquire such data. With this in mind, FIG. 1 illustrates an embodiment of an imaging system 10 for acquiring and processing image data in accordance with aspects of the present disclosure. In the illustrated embodiment, imaging system 10 is a computed tomography (CT) imaging system designed to acquire X-ray projection data, to reconstruct the projection data into a volumetric reconstruction, and to process the image data for display and analysis. The CT imaging system 10 includes one or more X-ray sources 12, such as one or more X-ray tubes or solid state emission structures which in combination allow X-ray generation at two or more spectra having different energy characteristics during the course of a material decomposition imaging examination. For example, the two or more spectra may differ in one or more of their mean, median, mode, maximum, or minimum X-ray energies. Thus, CT imaging system 10 may have: (a) a single X-ray source 12 which, natively or with applied filtration, generates X-rays at different times in accordance with two or more different energy spectra; (b) two (or more) different X-ray sources 12 which, natively or with applied filtration, generate X-rays in accordance with different energy spectra.

By way of example, in one embodiment an X-ray source 12 (e.g., an X-ray tube) may be switched between a relatively low energy polychromatic emission spectra (e.g., at about 80 kVp) and a relatively high energy polychromatic emission spectra (e.g., at about 140 kVp). As will be appreciated, the X-ray source(s) 12 may also be operated so as to emit X-rays at more than two different energy spectra, though dual-energy embodiments are discussed herein to simplify explanation. Similarly, the X-ray source(s) 12 may emit at polychromatic spectra localized around energy levels (i.e., kVp ranges) other than those listed herein. Indeed, selection of the respective energy levels for emission may be based, at least in part, on the anatomy being imaged and the chemical or molecules of interest for tissue characterization.

In certain implementations, the X-ray source 12 may be positioned proximate to a beam shaper 22 used to define the size and shape of the one or more X-ray beams 20 that pass into a region in which a subject 24 (e.g., a patient) or object of interest is positioned. The subject 24 attenuates at least a portion of the X-ray beam 20. Resulting attenuated X-rays 26 impact a detector array 28 formed by a plurality of detector elements (e.g., a one-dimensional or two-dimensional detector array). Each detector element produces an electrical signal that represents the intensity of the X-ray beam 20 incident at the position of the detector element when the X-ray beam 20 strikes the detector array 28. Electrical signals are acquired and processed to generate one or more scan datasets. As discussed in greater detail below, in certain embodiments the detector array 28 may have two or more distinct detection layers, such as a direct-conversion detector layer and a conventional scintillator-based (i.e., charge integrating or conversion-type) detector layer.

A system controller 30 commands operation of the CT imaging system 10 to execute examination protocols and to pre-process or process the acquired data. With respect to the X-ray source(s) 12, the system controller 30 furnishes power, focal spot location, control signals and so forth, for the X-ray examination sequences. The detector array 28 is coupled to the system controller 30, which commands acquisition of the signals generated by the detector array 28. In addition, the system controller 30, via a motor controller 36, may control operation of a linear positioning subsystem 32 and/or a rotational subsystem 34 used to move components of the CT imaging system 10 and/or the subject 24.

The system controller 30 may include signal processing circuitry and associated memory circuitry. In such embodiments, the memory circuitry may store programs, routines, and/or encoded algorithms executed by the system controller 30 to operate the CT imaging system 10, including the X-ray source 12 and detector array 28, and to process the data acquired by the detector array 28. In one embodiment, the system controller 30 may be implemented as all or part of a processor-based system such as a general purpose or application-specific computer system.

The X-ray source(s) 12 may be controlled by an X-ray controller 38 contained within the system controller 30. The X-ray controller 38 may be configured to provide power and timing signals to the X-ray source(s) 12. In addition, in some embodiments the X-ray controller 38 may be configured to selectively activate the X-ray source(s) 12 such that tubes or emitters at different locations within the CT imaging system 10 may be operated in synchrony with one another or independent of one another. In certain embodiments discussed herein, the X-ray controller 38 may be configured to provide fast-kVp switching of an X-ray source 12 so as to rapidly switch the kV at which the X-ray source 12 is operated to emit X-rays at different respective polychromatic energy spectra in succession during an image acquisition session. For example, in a dual-energy imaging context, the X-ray controller 38 may operate an X-ray source 12 so that the X-ray source 12 alternately emits X-rays at the two (e.g., low and high) polychromatic energy spectra of interest, such that adjacent projections are acquired at different energies (i.e., a first projection is acquired at high energy, the second projection is acquired at low energy, the third projection is acquired at high energy, and so forth).

The system controller 30 may include a data acquisition system (DAS) 40. The DAS 40 receives data collected by readout electronics of the detector array 28, such as sampled digital or analog signals from the detector array 28. The DAS 40 may then convert the data to digital signals for subsequent processing by a processor-based system, such as a computer 42. In other embodiments, the detector array 28 may convert the sampled analog signals to digital signals prior to transmission to the data acquisition system 40. As noted above, in certain embodiments the detector array 28 may include two or more distinct detection layers, such as a scintillator-based (i.e., energy-integrating) detector layer and a direct-conversion detector layer. In such embodiments, the DAS 40 may be configured to as to readout both layers of the detector array 28 and to provide both sets of data for processing.

In the depicted example, the computer 42 may include or communicate with one or more non-transitory memory 46 that can store data processed by the computer 42, data to be processed by the computer 42, or instructions to be executed by a processor of the computer 42. For example, a processor (e.g., image processing circuitry 44) of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein.

The computer 42 may also be adapted to control features enabled by the system controller 30 (i.e., scanning operations and data acquisition), such as in response to commands and scanning parameters provided by an operator via an operator workstation 48. The CT imaging system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the CT imaging system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote client 56, radiology department information system (RIS), hospital information system (HIS) or to an internal or external network, so that others at different locations can gain access to the image data.

As noted above, the X-ray source(s) 12 may be configured to emit X-rays at more than one energy spectrum. Though such emissions may be generally described or discussed as being at a particular energy (e.g., 80 kvP, 140 kVp, and so forth), the respective X-ray emissions at a given energy are actually along a continuum or spectrum and may, therefore, constitute a polychromatic emission centered at, or having a peak strength at, the target energy. For the purpose of material decomposition, such differing emission spectra allow attenuation data to be obtained for the same regions at the different spectra, thereby allowing differential attenuation at the different spectra to be determined for a given material (or volume of material). Based on this differential attenuation at the known spectra, material decomposition techniques may be applied.

From a theoretical perspective, it would be desirable for each individual X-ray photon to be detected, its energy determined and the respective measurement appropriately binned or otherwise characterized so as to provide infinite spectral separation. That is, for a given and known X-ray spectrum, the resulting attenuated spectrum could be accurately measured so that attenuation at each X-ray energy could be accurately characterized for each volumetric region traversed by the X-rays, allowing improved material decomposition within the imaged region.

In practice, CT detectors are not currently capable of discerning energy levels of individual X-ray photons in this manner. Instead, as noted above, different emission spectra are typically employed using conventional detection mechanisms such that differential measurements are obtained at the two spectra (i.e., high energy and low energy). For example, certain approaches employ two different X-ray sources 12 and corresponding detector arrays 28 such that there is a high energy X-ray source and a detector array and a separate low energy X-ray source and a detector array which can scan concurrently from offset angles. Such approaches may further employ an edge filter on one or both of the X-ray source and detector array combinations so as to further improve separation of the spectra. Such approaches however, even with filtration, still yield spectra that overlap over a significant portion of their range and, further, yield data that is poorly temporally registered due to the angular offset of the separate X-ray source and detector array pairs.

In other approaches, an X-ray source 12 may be rapidly switched between high and low energy emitting states, with the resulting X-ray emission detected on a detector array 28 opposite the X-ray source 12 with respect to the imaged volume. This type of approach also yield overlapping high- and low-energy spectra, which is not the ideal for material decomposition studies. However, one advantage to these approaches is that the acquired high- and low-energy measurements exhibit good temporal registration (i.e., high- and low-energy measures exist close in time to one another for a given view angle and tissue region).

In yet another approach a single X-ray source 12 emitting at a single spectrum may be employed in conjunction with a pair of conventional scintillator-based detectors. One of the scintillator-based detectors is generally configured for high-energy X-ray detection (such as due to a thicker scintillator) while the other is generally configured for low-energy X-ray detection (such as due to a thinner scintillator). In such an approach the detections are essentially characterized as high- or low-energy based on the detector a signal is measured at. However separation is poor due to some number of low-energy X-ray photons making it through to the high-energy detector and, conversely, some number of high-energy X-ray photons being stopped at the low-energy detector. Thus, there is still substantial overlap of the measured signals, and hence poor separation for material decomposition purposes.

With the preceding in mind, the present approaches relate to a detector array 28 having two or more X-ray detection layers, one of which is a conventional scintillator-based (i.e., energy-integrating) detection layer and the other of which is a direct-conversion (i.e., single photon-counting) type detection layer. In certain embodiments, such a detector array 28 may be used in conjunction with suitable multi- or dual-energy X-ray emission approaches, such as the use of separate and distinct high-energy and low-energy X-ray sources 12, the use of a single X-ray source 12 switched between high-energy and low-energy emitting states, the use of filters with one or more X-ray sources 12 to produce different energy spectra, and so forth.

In the direct-conversion type detector layer, a semiconductive sheet or layer of material (e.g., silicon (Si), germanium (Ge), gallium arsenide (GaAs), cadmium telluride (CdTe), cadmium zinc telluride (CZT), or any other suitable semiconductor) is provided which, in response to X-ray photon impact events generates a discrete charge without an intervening optical photon (or any other low-energy photon) conversion step (i.e., without an intervening scintillation step or the use of a scintillator material). Such discrete charges correspond to single X-ray photon impact events and may be readout and converted from an analog to a digital signal, such as at the detector or downstream. In such a direct-conversion process, each X-ray photon event impacting the detection layer may be detected and its energy measured, leading to these types of detectors being referred to as photon-counting detectors or single photon-counting detectors. The direct-conversion type detector layer, as discussed herein, may have resolution equal to or greater than that exhibited by the energy-integrating detection layer discussed below.

This is in contrast to the scintillator-based detection layer, where an X-ray impact event in a scintillator material leads to corresponding generation of a number of lower-energy photons (referred to herein as optical photons, even though this terminology as used within this document may encompass some wavelengths outside the conventional visible spectrum) which are measured over an array of some discrete areas (e.g., pixels) and over some time period called a view in a CT system, corresponding to elements of a light imager panel to give a single measure (i.e., number) representing X-ray intensity. That is, the pixels of the light imager accumulate charge between readout events and the respective accumulated charges, when readout, correspond to aggregated or integrated X-ray intensity at each of the respective pixels. Such detection mechanisms are typically characterized as energy-integrating approaches.

The benefit of combining or stacking an energy-integrating detection layer and a direct-conversion detection layer within a detector array 28 is the added spectral sensitivity in the direction X-ray photons travel in the imaging context. For example, in the stacked detection layer scenario discussed by way of example, the direct-conversion detection layer may be positioned so that it is impacted or crossed first by the X-ray photons (i.e., above the energy-integrating detection layer) and will generate a low-energy reading. That is, the thickness, density, and positioning of the direct-conversion detection layer will be more likely, in this scenario, to stop some portion (e.g., 10%, 20%, 30%, and so forth) of the low-energy X-ray photons, as opposed to higher energy photons which will be more likely to pass through. Thus, the direct-conversion detection layer will generate signals that generally correspond to low-energy X-ray detection events while the underlying energy-integrating detection layer will generate signals that generally correspond to high or higher-energy X-ray detection events.

Figure 2:
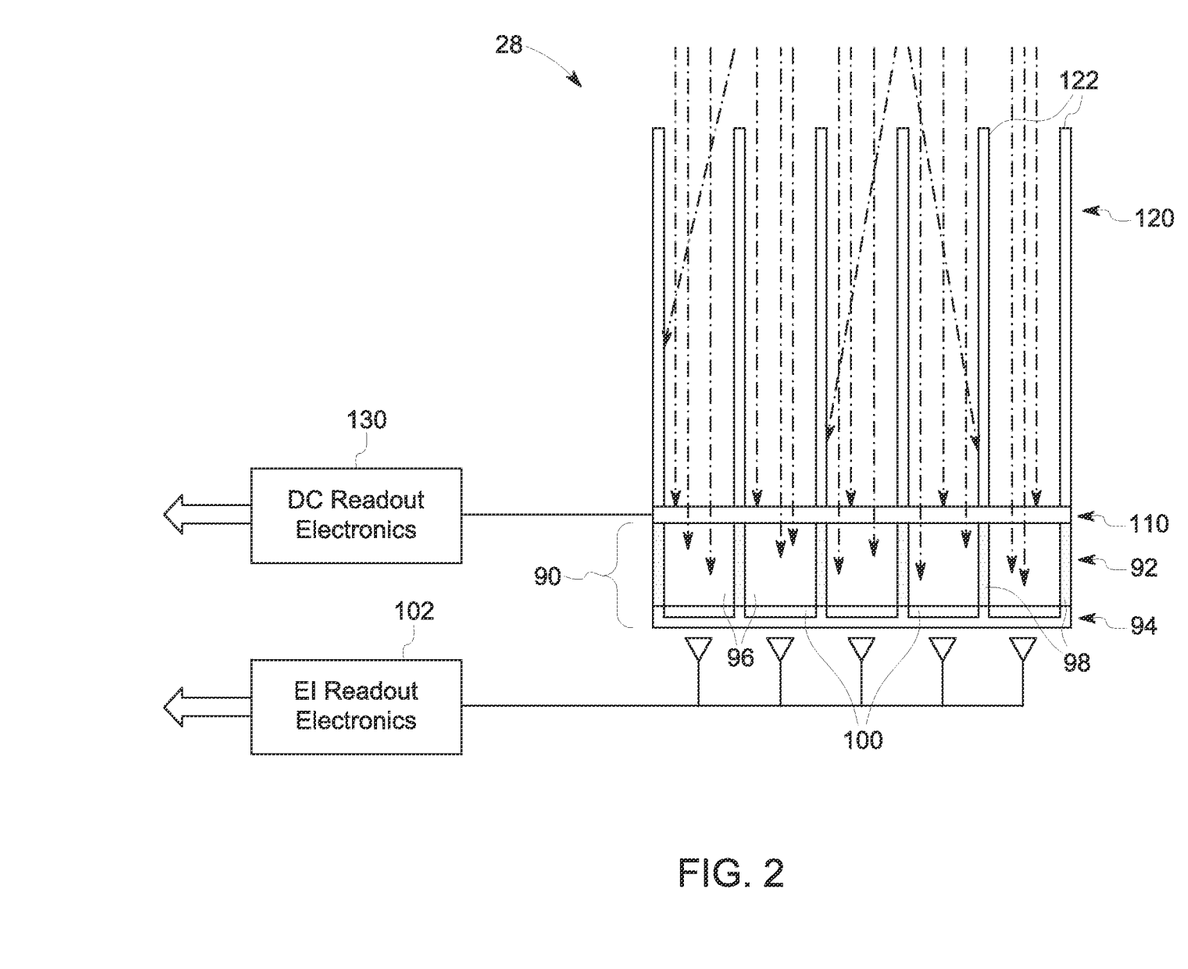
FIG. 2 is schematic cross-sectional view of a portion of an embodiment of an X-ray detector in accordance with aspects of the present disclosure.

By way of example, and turning to FIG. 2 a cross-sectional view of a portion of a detector array 28 is shown. In this example, the detector array 28 includes a conventional energy-integrating detection layer 90 that includes, among other components, a scintillator layer 92 and an imager (i.e., optical detection) layer 94 positioned proximate the scintillator layer 92 in the direction opposite of X-ray emission. The depicted detector array 28 also includes a direct-conversion detection layer 110, which may include a layer of semi-conductive material that generates spatially-localized charges in response to incident X-ray beam 20. Also shown in FIG. 2, though optional, is an anti-scatter grid or collimator 120 comprising X-ray opaque plates 122 positioned so as to absorb those X-rays 20 reflected or scattered in their passage through the imaging volume. When present the anti-scatter grid 120 ensures those X-ray photons reaching the direct-conversion detection layer 110 and the energy-integrating detection layer 90 have traveled straight through the imaging volume, as opposed to being scattered by the imaged object or imaging apparatus, thus reducing noise and artifacts attributable to scatter.

In the depicted example, prior to X-ray beam 20 reaching the scintillator layer 92 (but after collimation by the anti-scatter grid 120, if present), the X-rays 20 reach a direct-conversion detection layer 110 which as noted above, may be fabricated from one or more semiconductor materials (e.g., silicon (Si), germanium (Ge), gallium arsenide (GaAs), cadmium telluride (CdTe), cadmium zinc telluride (CZT), or combinations thereof). In response to an X-ray beam 20 impacting the direct-conversion detection layer 110, a spatially-localized charge is generated (without a scintillation or other conversion step) which is read out by the direct-conversion (DC) readout electronics 130. The spatial location and /or extent of the readout charge may then be used in downstream image reconstruction (such as to generate an image or volumetric representation) or image processing (such as to facilitate subtractive imaging, material decomposition processing, contrast enhancement, and so forth).

As shown in the example of FIG. 2, only a subset of the X-ray beam 20 are stopped by the direct-conversion detection layer 110, with the remainder proceeding to the conventional, energy-integrating detection layer 90 underlying the direct-conversion detection layer 110. As a result, detection events occurring at the direct-conversion detection layer 110 will generally correspond to spectrally low-energy (i.e., less penetrating) X-ray photons, with the detection events occurring at the energy-integrating detection layer 90 generally corresponding to spectrally higher-energy X-ray photons. In practice, the thickness and/or composition of the direct-conversion detection layer 110 will determine the spectrum or energy level of X-ray photons 20 stopped by the direct-conversion detection layer 110 (e.g., 1 mm-10 mm of silicon (Si), 0.2 mm-1 mm germanium (Ge), 0.2 mm-1 mm gallium arsenide (GaAs), 0.2 mm-1 mm cadmium telluride (CdTe), 0.2 mm-1 mm cadmium zinc telluride (CZT) may be most appropriate but any other thicknesses could also be used). Thus, the ordering of the detection layers, the thickness of the direct-conversion detection layer 110, and/or the composition of the direct-conversion detection layer 110 may be configured or designed to achieve a desired energy spectrum or energy band being stopped at the direct-conversion detection layer 110 and a corresponding efficiency associated with stopping the desired energy X-ray photons 20.

With respect to the energy-integrating detection layer 90, the scintillator layer 92 may be pixelated, as shown in the example of FIG. 2, with discrete elements or regions of scintillating material 96 bounded by pixel boundaries 98 which act to limit cell-to-cell cross talk generated in a region of the scintillating material 96 to detection by a corresponding pixel 100 of the imager layer 94. Thus, the pixel boundaries 98 generally do not allow transmission of optical photons between pixelated regions of the scintillator layer 92 and may be reflective or non-reflective. Though a pixilated scintillator layer 92 is illustrated in the example of FIG. 2, it should be appreciated that other types of scintillator layers 92, including those with no structural pixilation elements or boundaries, may also be employed in a detector array 28 as discussed herein.

With respect to the imager layer 94, such a layer may include an array of photodetector elements arranged as pixels 100. By way of example, the photodetector elements may be an array of photodiodes, with each respective photodiode accumulating charge when an area corresponding to a respective pixel 100 is exposed to optical photons generated in the scintillator layer 92. These accumulated charges, in such an embodiment, are periodically readout to obtain measures of the incident X-ray energy observed at each pixel 100 and the respective photodiode reset for the next readout cycle. In the illustrated example, readout is performed using energy-integrating (EI) readout electronics 102, which may take advantage of an arrangement of sequential scan lines and data lines to address and readout individual pixels during a readout operation.

Signals acquired by the EI readout electronics 102 and/or DC readout electronics 130 may be provided to downstream processing components for analog-to-digital conversion (if not performed in the readout electronics), pre-processing (e.g., gain correction, bad pixel correction, noise reduction, and so forth), and/or image processing (including artifact correction operations, image reconstruction and so forth). The increased spectral resolution and discrimination provided by both detection layers improves various aspects of multi-energy, as well as other, imaging techniques. With the preceding in mind, the associated readout results from the DC readout electronics 130 and EI readout electronics 102 in combination can be combined in downstream image processing to generate images that take advantage of the multi-energy or spectral data, such as material decomposition imaging, contrast imaging or enhancement, vascular tree and/or soft tissue volume reconstruction, and so forth. Examples of benefits associated with acquiring both the direct-conversion and energy-integrating detection data over a volume of interest using one or more energy spectra include, but are not limited to: improved contrast (e.g., iodine) conspicuity; improved spectral power, improved energy separation; improved dose efficiency; improved k-edge imaging material decomposition on demand; high resolution performance using the direct-conversion detection layer 110; good low-signal performance; and reduced high energy noise.

In one embodiment, the usefulness and/or completeness of the data acquired using a detector array 28 having both a direct-conversion detection layer 110 and an energy-integrating detection layer 90 can be further improved by using a fast-switching X-ray source 12 (i.e., an X-ray source 12 that switches between emitting high- and low-energy spectra at each respective view angle) with high temporal resolution and good temporal registration at each view angle imaged. For example, in conjunction with such a fast-switching X-ray source 12, data will be acquired at each view angle at both a high- and low-energy spectrum and using both the direct-conversion detection layer 110 and energy-integrating detection layer 90 for each energy spectrum. Thus, high- and low-energy discrimination can be achieved and increased by use of both a switched X-ray source 12 and a high- and low-energy discriminating detector array 28.

Figure 3:
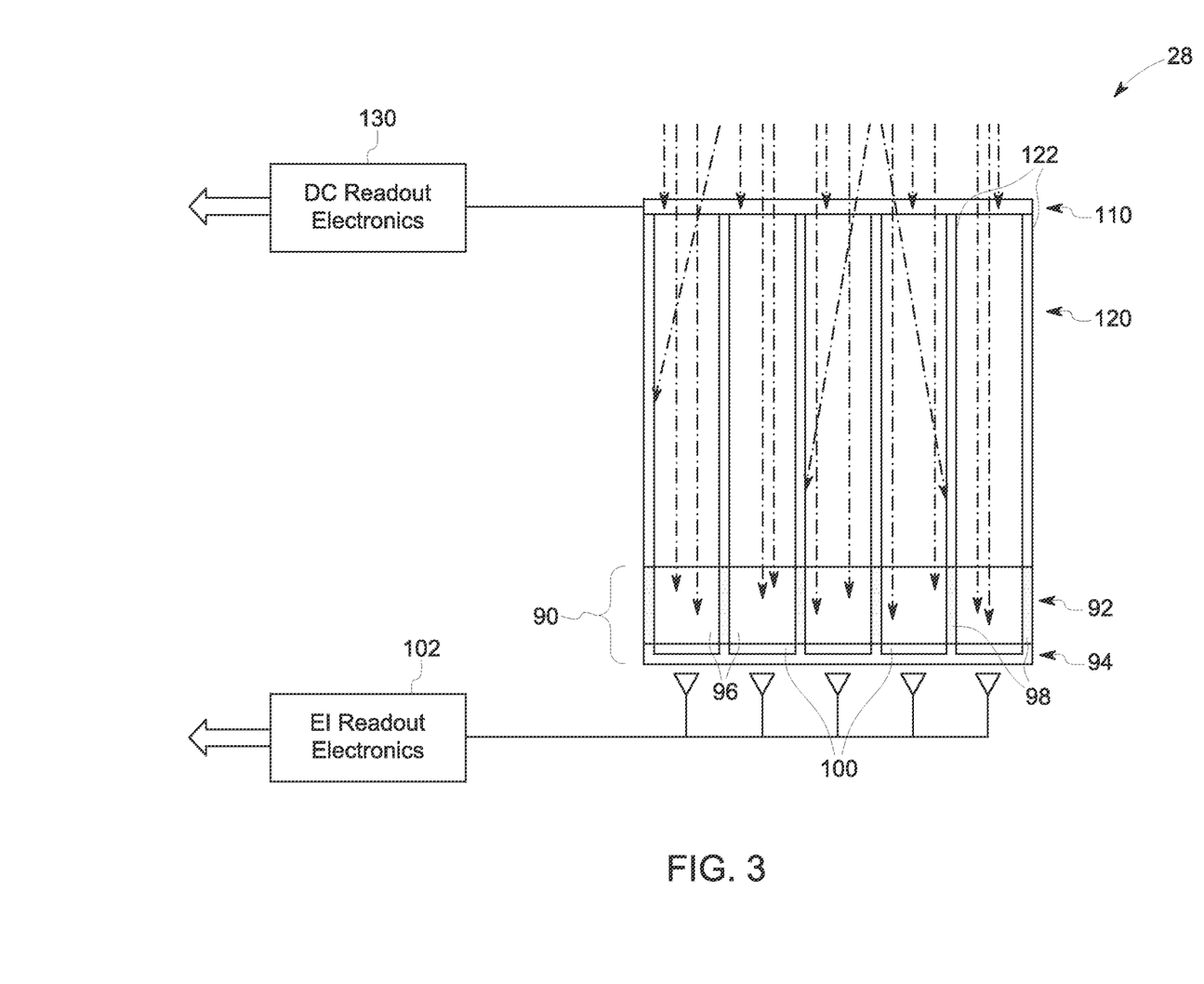
FIG. 3 is schematic cross-sectional view of a portion of a further embodiment of an X-ray detector in accordance with aspects of the present disclosure.

In other embodiments, the configuration of the components discussed with respect to FIG. 2 may be rearranged to accommodate particular contexts or scenarios. For example, turning to FIG. 3, in certain contexts it may be desirable to add the functionality described above to an existing, conventional energy-integrating detector. In such a scenario, the direct-conversion detection layer 110 may be added as an add-on. retrofit, or upgrade component. In such an embodiment, as shown in FIG. 3, the direct-conversion detection layer 110 may be positioned outside or on top of the anti-scatter grid 120, which may be formed integral with the energy-integrating detection layer 90. Thus, the direct-conversion detection layer 110 may be added to an existing detector array 28 having an energy-integrating detection layer 90 as an add-on piece to provide the added functionality noted above.

Figure 4:
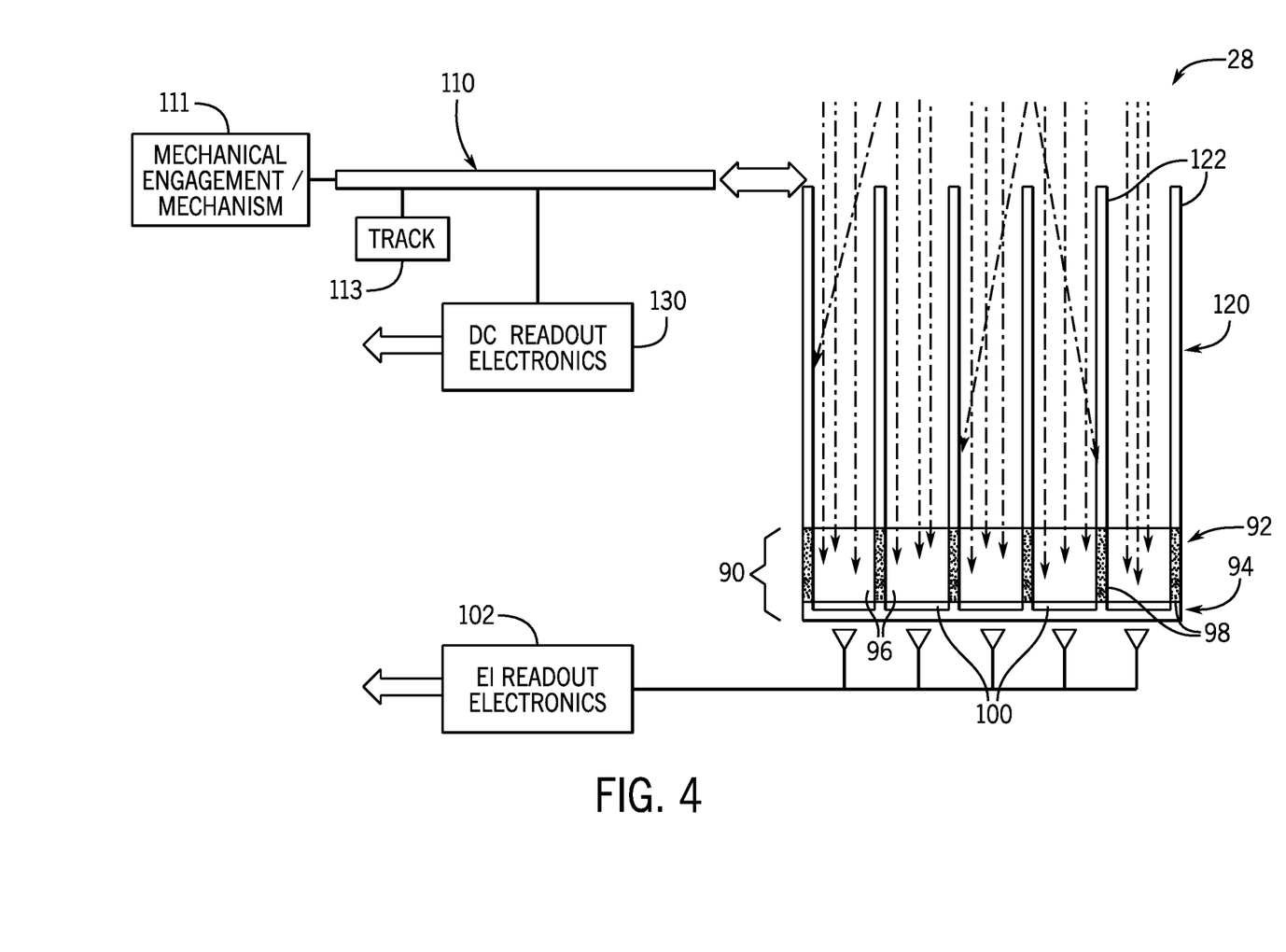
FIG. 4 is schematic cross-sectional view of a portion of another embodiment of an X-ray detector in accordance with aspects of the present disclosure.

Further, turning to FIG. 4, in some embodiments the direct-conversion detection layer 110 may be configured to be moved in and out of the X-ray path, such as along the z-direction corresponding to the axis about which the gantry rotates. For example, based on the imaging needs associated with a give scan protocol the direct-conversion detection layer 110 may be moved into or out of the detection mechanism (e.g., the detector 28) based on an automated (e.g., in response to the selected scan protocol) or user-implemented (e.g., in response to a user-input) instruction. Movement of the direct-conversion detection layer 110 may be by a mechanical engagement 111 that moves the direct-conversion detection layer 110 along a set track 113 or other path to place the direct-conversion detection layer 110 into the X-ray path for some scans (such as material decomposition, dual energy, contrast enhanced, and so forth) but not for others. In this manner, the detector 28 may utilize only energy-integrating detection for those scans where the additional data provided by the direct-conversion detection layer 110 is not necessary and/or helpful.

While the preceding discussion has generally described embodiments employing a single direct-conversion detection layer 110 to simplify explanation and to otherwise facilitate understanding, in other embodiments, more than one direct-conversion detection layer 110 may be provided. In such embodiments, the separate direct-conversion detection layers 110 may differ in one or both of thickness and/or composition, but even if otherwise identical would still provide additional spectral information based on the different respective positioning within the detector stack (i.e., the direct-conversion layer reached first by the X-rays 20 would be associated with lower-energy X-ray events, and so forth). Likewise, as with the example discussed in FIG. 4, one or more of the direct-conversion detector layers 110 may be configured to be removed based on the selected san protocol and the quantity and/or quality of spectral data that would benefit the selected scan.

Figure 5:
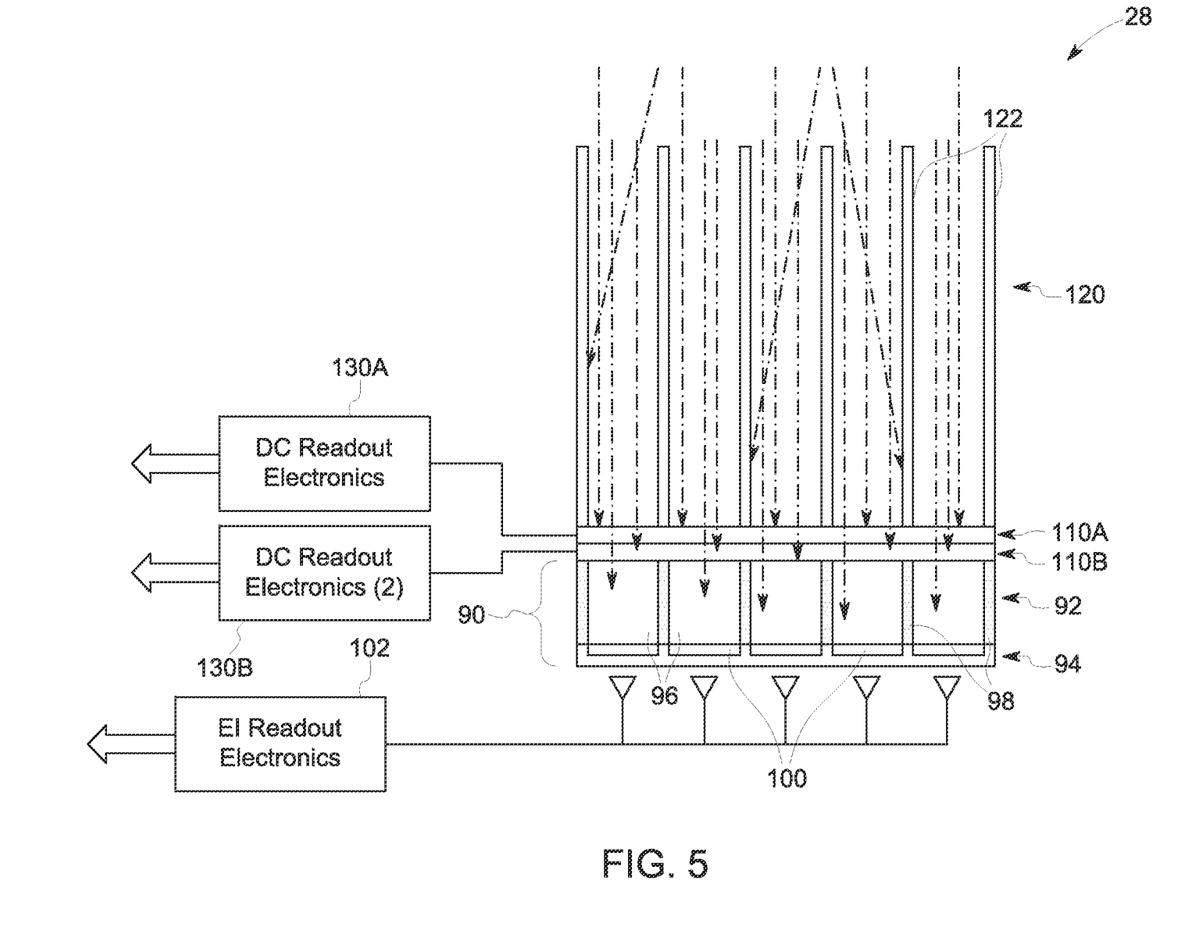
FIG. 5 is schematic cross-sectional view of a portion of a further embodiment of an X-ray detector in accordance with aspects of the present disclosure.

By way of example, and turning to FIG. 5, a detector array 28 is shown having a first direct-conversion detection layer 110A and a second direct-conversion detection layer 110B vertically stacked within the detector array 28. The first direct-conversion detection layer 110A and the second direct-conversion detection layer 110B may differ in one or both of thickness or composition or may differ only with respect to their respective placement within the detector array 28. Both the first direct-conversion detection layer 110A and the second direct-conversion detection layer 110B yield separate and distinct spectral X-ray data based on the respective X-ray photon impact events occurring within the respective layers. In the depicted example each of the first direct-conversion detection layer 110A and the second direct-conversion detection layer 110B have separate direct-conversion readout electronics, 130A and 130B respectively, though in other embodiments the readout electronics may be shared between the respective direct-conversion detection layers. As will be appreciated, though only two layers 110A, and 110B are illustrated, in other embodiments additional direct-conversion detection layers 110 (e.g., 3, 4, 5, 6, and so forth) may be provided within a given detector array 28.

Figure 6:
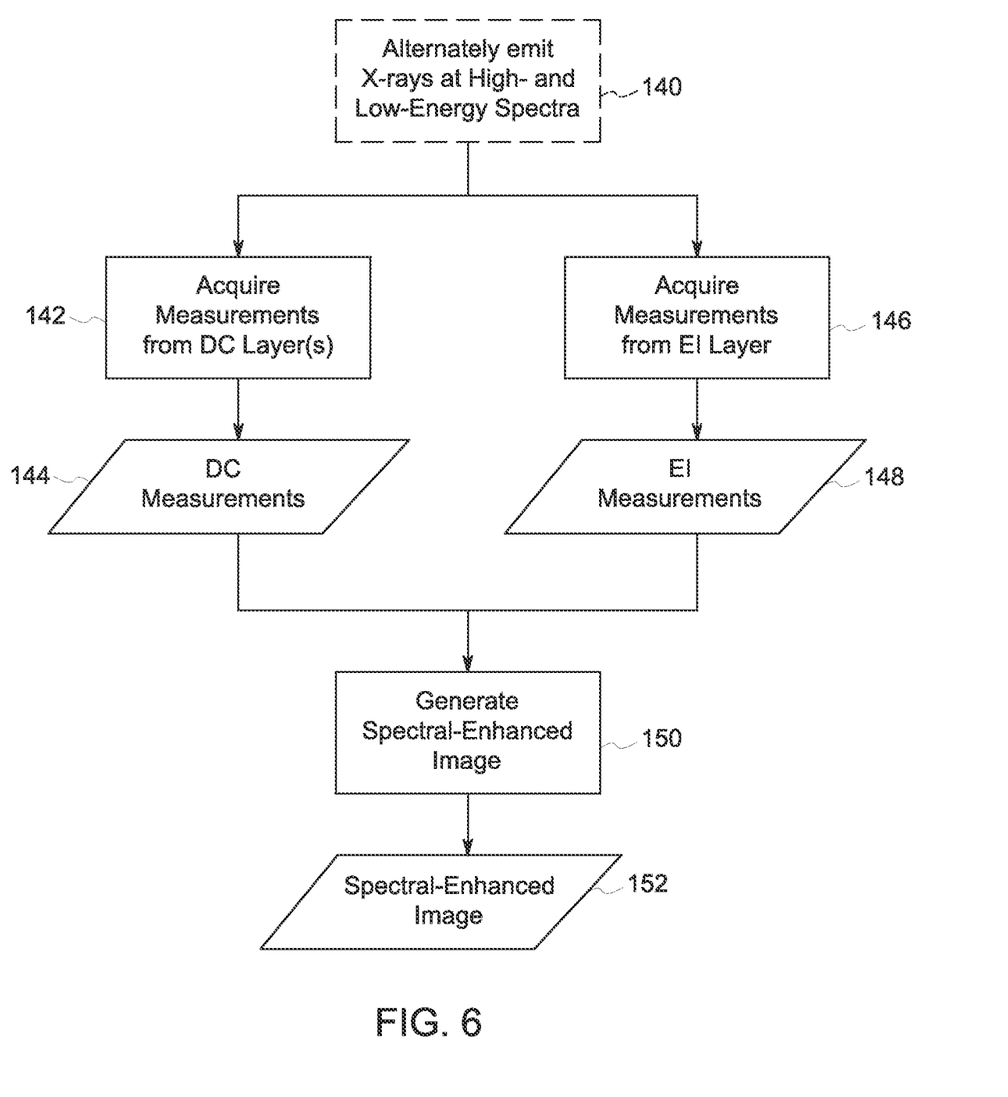
FIG. 6 is a process flow of an X-ray detection technique in accordance with aspects of the present disclosure.

With the preceding in mind, FIG. 6 depicts a high-level overview of an implementation of a scan procedure performed using a detector array 28 as discussed herein. As will be appreciated, different scan protocols may involve different pre-processing and processing steps, which are not represented in this high-level figure. However, FIG. 6 depicts steps generally believed to be in common to those scan protocols performed using a detector array 28 as discussed herein.

In a first step, X-rays are emitted (Block 140) toward the detector array 28 though an imaging volume of interest (e.g., a patient). In certain embodiments, X-rays are emitted at a single energy spectrum, with spectral information gleaned from the measurements of the energy-integrating detection layer and from the direct-conversion detection layer. In other, X-rays are emitted at two or more energy spectra, with spectral information gleaned from both the emission spectra and the measurements of the energy-integrating detection layer and from the direct-conversion detection layer. By way of example, FIG. 6 depicts the emission step 140 as optionally being performed by a fast-switching X-ray source that emits X-rays at both high- and low-energy spectra for each view angle of interest. Such an approach provides temporally registered measurements at both high- and low-energy spectra for each view of interest.

Measurements (Blocks 144, 148) are acquired from both the direct-conversion detection layer(s) 110 (Block 142) and the energy-integrating detection layer 90 (Block 146). In the instance where measurements are acquired for a single emission spectrum, the measurements 144, 148 will constitute two sets of measurements for the single emission spectrum. Conversely, in instances where measurements are acquired for two different emission spectra (e.g., high- and low-energy spectra), the direct-conversion detection measurements 144 will be acquired for each respective spectrum and energy-integrating detection measurements 148 will be acquired for each respective spectrum.

In the depicted example, the respective direct-conversion measurements 144 and energy-integrating measurements 148 are used in the generation (Block 150) of an image 152 that benefits from the spectral data proved by the respective measurements 144, 148. Examples of such spectrally-enhanced or benefited images 152 may include, but are not limited to material decomposition images, soft tissue images, vascular tree reconstructions, contrast-enhanced images, and so forth. By way of further example, improvements to material differentiation techniques when using a detector array 28 as described herein include, but are not limited to: improved contrast (e.g., iodine) conspicuity (e.g., ~2x the conspicuity for an equivalent dose); improved material differentiation (e.g., ~4x compared to dual kVp with single layer energy-integrating detectors and ~10x compared to single kVp with dual energy-integrating detector layers); and improved performance with respect to k-edge type imaging or contrast materials or agents (e.g., k-edge materials that take advantage of the k-edge discontinuity in spectral imaging). Other potential benefits of the detector array 28 as described herein include, but are not limited to: improved low signal performance (i.e., minimal electronic noise), improved does efficiency, improved resolution (i.e., smaller element (i.e., pixel) size with respect to the direct-conversion detection layer 110), and the ability to fabricate patterned detectors using conventional semiconductor fabrication approaches.

Technical effects of the invention include a radiation detector having an energy-integrating detection layer 90 and at least one direct-conversion detection layer 110. In certain embodiments, the direct-conversion detection layer 110 is impacted first by an incident X-ray beam, such that X-ray photons stopped at the direct-conversion detection layer 110 are generally lower in energy than those which reach the energy-integrating detection layer 90. The data acquired using the direct-conversion detection layer 110 and energy-integrating detection layer 90 may be combined to provide additional spectral discrimination, such as in material decomposition or contrast-enhancement applications. In certain embodiments, the direct-conversion detection layer 110 may be a retro-fitted addition to an existing energy-integrating detector. In addition, in some embodiments, the direct-conversion detection layer 110 may be a movable component that is moved into the X-ray path for scan protocols that would benefit from the additional energy separation data but not for protocols that would not benefit from the additional energy separation data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A radiation detector, comprising:
an energy-integrating detection layer comprising:
a scintillator layer that generates optical photons when exposed to a beam of X-rays; and
an imager layer positioned to generate a first set of measurements when exposed to optical photons generated by the scintillator layer;
a direct-conversion detection layer configured to generate a second set of measurements when exposed to the beam of X-rays, wherein the direct conversion detection layer is positioned relative to the energy-integrating detection layer so as to be impacted by the beam of X-rays before the energy-integrating detection layer;
an anti-scatter grid positioned between the direct-conversion detection layer and the energy-integrating detection layer so as to absorb scattered X-rays prior to reaching the energy-integrating detection layer; and
an additional direct-conversion detection layer configured to respectively generate additional sets of measurements when exposed to the beam of X-rays, wherein the additional direct-conversion detection layer directly contacts the direct-conversion detection layer.
2. The radiation detector of claim 1, wherein the direct-conversion detection layer comprises a semiconductive layer of one or more of silicon (Si), germanium (Ge), gallium arsenide (GaAs), cadmium telluride (CdTe), cadmium zinc telluride (CZT), or any other suitable semiconductor material.

3. The radiation detector of claim 1, wherein the direction-conversion detection layer and the additional direct-conversion detection layer differ in thickness, composition, or both thickness and composition.

4. The radiation detector of claim 1, wherein the direction-conversion detection layer and the additional direct-conversion detection layer yield separate and distinct spectral X-ray data from each other.

5. An imaging system, comprising:
one or more X-ray sources configured to emit X-rays across an imaging volume;
an X-ray detector comprising at least:
an energy-integrating detection layer configured to generate a first set of measurements in response to emitted X-rays;
a direct-conversion detection layer configured to generate a second set of measurements in response to emitted X-rays, wherein a resolution of the direct-conversion detection layer is equal to or better than a resolution of the energy-integrating detection layer; and
an anti-scatter grid positioned between the direct-conversion detection layer and the energy-integrating detection layer so as to absorb scattered X-rays prior to reaching the energy-integrating detection layer;
a system controller configured to control operation of the one or more X-ray sources and the X-ray detector; and
one or more processor-based components configured to generate images using both the first set of measurements and the second set of measurements;
wherein the direct-conversion detection layer is configured to be movable out of a path of a beam of X-rays so that the beam of X-rays only impacts the energy-integrating detection layer when the direct-conversion detection layer is so moved,
wherein the imaging system further comprises a track and a mechanical mechanism configured to move the direction-conversion detection layer along the track into and out of the path of the beam of X-rays.

6. The imaging system of claim 5, wherein the one or more X-ray sources comprise an X-ray tube configured to be switched between a first X-ray emission spectrum and a second X-ray emission spectrum.

7. The imaging system of claim 6, wherein the second X-ray emission spectrum is a lower energy spectrum relative to the first X-ray emission spectrum and where the second set of measurements corresponds substantially to X-rays emitted at the lower energy spectrum.

8. The imaging system of claim 5, wherein the energy-integrating detection layer comprises a scintillator and a light imager panel.

9. The imaging system of claim 5, wherein the direct-conversion detection layer comprises a semiconductive layer of one or more of silicon (Si), germanium (Ge), gallium arsenide (GaAs), cadmium telluride (CdTe), cadmium zinc telluride (CZT), or any other suitable semiconductor material.

* * * * *